United States Patent [19]

Nöth et al.

[11] Patent Number: 4,739,096

[45] Date of Patent: Apr. 19, 1988

[54] PROCESS FOR PRODUCING CATECHOLBORANE

[75] Inventors: Heinrich Nöth, Grünwald; Detlef Männig, Munich, both of Fed. Rep. of Germany

[73] Assignee: Metallgesellschaft Aktiengesellschaft, Frankfurt am Main, Fed. Rep. of Germany

[21] Appl. No.: 894,329

[22] Filed: Aug. 7, 1986

[30] Foreign Application Priority Data

Aug. 7, 1985 [DE] Fed. Rep. of Germany ....... 3528321

[51] Int. Cl.$^4$ ........................... C07F 5/04; C07F 5/05; C07F 5/02
[52] U.S. Cl. ..................................... 558/288; 558/290
[58] Field of Search ................................ 558/288, 290

[56] References Cited

U.S. PATENT DOCUMENTS 3,361,672 1/1968 Andress, Jr. et al. ........... 558/290 X
3,920,701 11/1975 Kawashima et al. ............ 558/290 X

OTHER PUBLICATIONS

Chemical Abstracts 78:84451u, (1973).
Chemical Abstracts 104, 148952y, (1986).
Chemical Abstracts 96, 34374x, (1982).
Journal of the American Chemical Society, vol. 97, pp. 5249–5255, (1975).

*Primary Examiner*—Paul F. Shaver
*Attorney, Agent, or Firm*—Karl F. Ross; Herbert Dubno; Jonathan Myers

[57] ABSTRACT

A process is described in which catecholborane is produced by a reaction of a phenolic compound with a boron hydride in a solvent. Tris(catecholato)bisborane, i.e. the ester of boric acid and catechol, is reacted with an alkali metal-boron hydride in an aliphatic ether. A lithium halide is suitably used too, where sodium-boron hydride or potassium-boron hydride is employed. In a preferred embodiment, the reaction is carried out in conjunction with an activating grinding operation.

10 Claims, No Drawings

PROCESS FOR PRODUCING CATECHOLBORANE

CROSS REFERENCE TO RELATED APPLICATION

This application is related to our commonly owned copending application Ser. No. 894,292, filed Aug. 7, 1986.

FIELD OF THE INVENTION

Our present invention relates to a process for producing catecholborane by reacting a phenolic compound with a boron hydride in an organic solvent.

BACKGROUND OF THE INVENTION

It is known that catecholborane (1,3,2-benzodioxaboro-lane) can be used as a monofunctional hydroboronizing agent for alkenes and alkynes.

Catecholborane is produced in a known manner by the reaction of catechol (1,2-dihydroxybenzene) with borane in tetrahydrofurane (THF) below room temperature in accordance with the reaction equation 1:

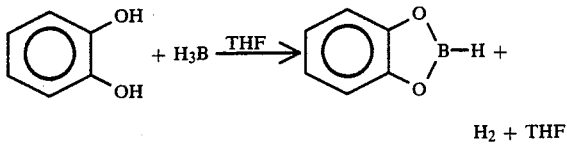

$H_2$ + THF (*Journal of the American Chemical Society*, Vol. 97, 1975, page 5249–55).

But this process has the disadvantage that two mole equivalents of the hydride are lost as is apparent from equation (1).

Moreover, considerable difficulties are encountered particularly in the isolation of the catecholborane from the solution with a high yield.

OBJECT OF THE INVENTION

It is an object of the invention to provide an improved process for the production of catecholborane which has a high yield in a solution or enables the isolation of the catechol with a high yield from solutions.

DESCRIPTION OF THE INVENTION

In the process of the invention for producing catecholborane, a specific phenolic compound is reacted with a boron hydride in a solution, i.e. tris(catecholato)-bisborane (ester of boric acid and catechol) is reacted in an aliphatic ether in accordance with equation (2).

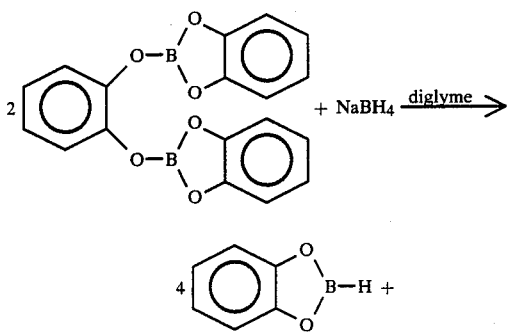

-continued

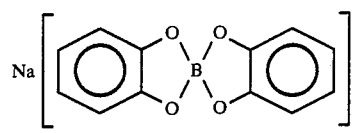

In accordance with the invention, the reaction is carried out at room temperature and reactants which can be handled in a simple manner are provided. Small amounts of diborane are formed by a secondary reaction.

In the process in accordance with the invention the reactants are used in substantially stoichometric ratio in a solvent. A high yield of catecholborane will be obtained if a ratio of alkali metal-boron hydride to boric acid ester of 1:2 is maintained. Diborane will be obtained in a high yield, if that ratio is increased to 3:2.

The alkali metal-boron hydride which is used can be lithium-boron hydride, sodium-boron hydride or potassium-boron hydride, or mixtures thereof, and preferably consists of sodium-boron hydride. The selection of the aliphatic ether depends on the requirements to be met for the desired further use of the catecholborane, i.e. on whether it is used in a known manner in a solution or in an isolated form for a hydroboronization in a known manner.

Suitable aliphatic ethers include dialkyl ethers having lower alkyl groups, such as diethyl, diisopropyl or dibutyl ethers, as well as the dimethyl or diethyl ethers of ethylene glycol, diethylene glycol or triethylene glycol. Cyclic ethers, such as tetrahydrofurane, or aromatic ethers, such as anisol may also be used as a solvent. The ethers may be used individually or as mixed ethers. For instance, the diethylene glycol dimethyl ether can suitably be used as a reaction medium if the catecholborane is to be used further in the reaction medium.

However, it is particularly desirable to react the reactants in a simple ether having lower alkyl groups, such as diethyl ether, diisopropyl ether or dibutyl ether. A particularly desirable reaction will be achieved by the use of diethyl ether. Because sodium borotetrahydride (NaBH$_4$) and potassium borohydride (KBH$_4$) have only a very low solubility in diethyl ether, a solubilizer is suitably employed. Suitable solubilizers include lithium halides, particularly lithium chloride. In that case, lithiumborohydride is formed by an intermediate reaction. Lithium chloride, which is readily soluble in diethyl ether, is generally added in an amount of 5 mole percent to the reaction mixture consisting of sodiumborohydride or potassium borohydride and of tris(catecholato)-bisborane. Smaller amounts and larger amounts, up to stoichiometric amounts may be used. The reaction will take place at room temperature under vigorous agitation.

The sodiumborohydride used for the reaction in simple diethyl ethers is suitably activated by being ground. In a particularly preferred embodiment of the invention the activating grinding operation is effected during the reaction. That operation can be carried out, e.g. in attrition mills or rod mills. In that embodiment of the process in accordance with the invention, yields between 75% and 95% are achieved and the catecholborane reaction product can be recovered in a simple manner in that the diethyl ether is distilled off. The catecholborane is isolated by a fractional distillation and is recovered in a yield of about 75 to 80% in pure form at about 75° C. and 100 torrs.

The advantages afforded by the process in accordance with the invention reside particularly in the provision of a method for producing catecholborane in a simple manner and for its isolation. Catecholborane is used as a selective hydroboronizing reactant and as an agent for producing diborane.

SPECIFIC EXAMPLES

The invention will be illustrated in greater detail with reference to the following Examples:

EXAMPLE 1

(a) Production of Tris(catecholato)bisborane (ester of boric acid and catechol)

In a Dean-Stark apparatus, 189 g catechol (1.71 moles) and 39.5 g $B_2O_3$ (0.57 mole) in 200 ml benzene or toluene are heated under reflux until the required amount of water (31 ml) has been driven off. This is the case after about 20 hours. A major part of the solvent is removed by distillation and the balance by vacuum distillation. Under the vacuum, a trace of solids sublimes within 2 hours at 150° C. The residue is then distilled and a small amount (about 10 ml) of the first runnings is discarded. Yield: 185 g (93%); boiling point 176°–177° C. at $7 \times 10^{-2}$ torr.

The boric acid ester may alternatively be produced by a reaction of boron oxide ($B_2O_3$) and catechol in a molten bath.

A distillation to isolate the boric acid ester is not required for its further processing.

(b) Further Processing of Catecholborane

A solution of 1.29 g $NaBH_4$ (34.1 millimoles) in diglycol dimethyl ether (diglyme) is added at room temperature to a solution of 23.64 g tris(catecholato)bisborane (68.3 millimoles) in 20 ml diglyme. The reaction mixture is stirred and is maintained under a nitrogen atmosphere formed by a nitrogen stream slowly flowing over the reaction mixture. Diborane ($B_2H_6$) which has formed is entrained by the nitrogen stream and is absorbed in acetone.

After the mixture has been stirred under the nitrogen atmosphere for 12 to 15 hours, 37 ml of a 3.6-molar solution of catecholborane in diglyme (yield 97%) are recovered by a distillation at a temperature of 80° to 100° C. and under a pressure of 100 torrs.

The nonvolatile residue is dried at a temperature of 100° C. and a pressure of $10^{-2}$ torr. By a comparison of the $^{11}B$ NMR spectrum of the residue ($\delta^{11}B$ 14.6 ppm in diglyme) with the $^{11}B$ NMR spectrum, of an authentic substance produced from catechol and sodium-boron hydride, the residue is identified to consist of sodium bis(catechol)borate, $NaB\text{-}(O_2C_6H_4)_2$.

EXAMPLE 2

185 g tris(catecholato)bisborane (0.53 mole) and 10.1 g sodium-boron hydride (0.27 mole) are charged into a ball mill, which contains steel balls. 400 ml diethyl ether and subsequently 570 mg lithium chloride are added and the reaction mixture is caused to react for 55 hours and is ground at the same time. The volatile components are then removed under a vacuum with the aid of a water bath. The fractional distillation of the condensate at 75° to 76° C. and 100 torrs resulted in a recovery of 99 g catecholborane (yield 78%).

EXAMPLE 3

Hydroboronizing using catecholborane as made by Example 1 or Example 2.

(A) Catalytic Hydroboronization of Olefins

In a three-necked 50 ml flask provided with a magnetic stirrer, a dropping funnel, a thermometer, a reflux condenser and a nitrogen inlet port, the olefin (45 millimoles) was dissolved in 7.5 ml benzene and 20.8 mg (0.05 mole percent) $[(C_6H_5)_3P]_3RhCl$ were added. Catecholborane was added in a stoichiometrically equivalent quantity to the red solution being stirred during a period of 10 to 20 minutes. The reduction is exothermic and may result in a boiling of the benzene. After 25 minutes, a distillative separation was effected, by which the 2-organyl-benzo-1,3,2-dioxaborolane is isolated.

The results of that reduction reaction performed with a number of olefins are compiled in the following Table. The yield has not been optimized.

| Substrate | Yield % | B.p., °C./torr | $\delta^{11}B$ (ppm) |
|---|---|---|---|
| 1-octene | 77.7 | 96–97/0.12 | 35.8 |
| Norbornene | 77.8 | 94/0.01 | 35.5 |
| Cyclopentene | 83.3 | 62/0.01 | 36.9 |
| Cyclohexene | 21.5[a] | 71/0.01 | 35.4 |
| 2,4,4-trimethyl-1-pentene | 5.8[b] | 96/0.08 | 35.4 |
| 3-vinyl-cyclohexene | 50.0[c] | 83/0.1 | 35.7 |

[a] 50% conversion after 4 days
[b] About 50% conversion after 2 days
[c] Reaction only at the vinyl group
Similar results, after longer reaction times, are obtained with ruthenium(II) chloride complex compounds such as $[(C_6H_5)P]_3Ru(CO)ClH$ or $[(C_6H_5)_3P]_3RuCl_2$.

(B) Catalytic Hydroboronization of Unsaturated Ketones

The procedure is the same as that described in (A). The reactants are used in the following quantities: 22.5 millimoles of the substrate and of the catecholborane, 0.05 mole percent tris(triphenylphosphine)rhodium(I) chloride and 70 ml benzene. The reaction mixture was stirred for 1 to 2 hours and was then separated by distillation.

| Substrate | Catalyst[a] | B—R : B—OR[a] | Yield %[b] | B.p., °C./torr | $\delta^{11}B$ ppm |
|---|---|---|---|---|---|
| (CH₂=CH–CH₂–CH₂–C(=O)–) | − | 0:100 | 75.8 | 74/0.08[c] | 23.2[c] |
| | + | 83:17 | 53.8 | 102/0.09[d] | 35.7[d] |

| | Catalyst[a] | | | | |
|---|---|---|---|---|---|
| Substrate | 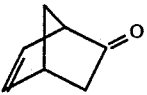 B—R |  B—OR[a] | Yield %[b] | B.p., °C./torr | δ$^{11}$B ppm |
| 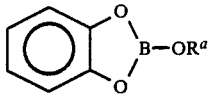 | −<br>+ | 0:100<br>83:17 | 92.0<br>76.7 | 96–97/0.1[c]<br>124/0.02[d] | 23.3[c]<br>35.5[d] |

[a] [11]B conversion ratio determined by NMR spectroscopy
[b] Related to isolated product
[c] Stated for BO3 product
[d] Stated for CBO2 product (C) Catalytic Hydroboronization of a Nitrile A solution of 5.0 ml catecholborane (45 millimoles) in 10 ml benzene was added in drops and with cooling with ice to a solution of 3.62 ml allyl cyanide (45 millimoles) and 208 kg tris(triphenylphosphine)rhodium(I) chloride in 20 ml benzene. After 5 hours, an almost complete conversion was revealed by a $^{11}$B NMR spectrum of the solution. The ratio of the CBO2 product to the NBO2 product amounted to 88:12. The solvent was withdrawn after 6 hours and was then distilled in a vacuum. The yield of the hydroboronized product A+B having a C=C double bond amounted to 4.05 g (48.1%). That product had a boiling point of 102° C. at 0.07 torr.

$\delta^1H(CDCl_3)$ 7.2–6.9 m (8H); 2.6–2.2 m (4H); 2.0–1.7 m (3H); 1.4–1.2 m (5H).

$\delta^{13}C(CDCl_3)$ 147.3; 122.0; 118.9; 111.6; 19.3; 14.04; 9.1 (br) about 60%, 147.2; 122.2; 118.6; 118.8; 19.2; 18.2; 9.1 (br) about 40%.

$\delta^{11}B(CDCl_3)$ 34.9 h ½=670 Hz.

When the same reaction is carried out without a catalyst, an $^{11}$B NMR spectrum of the solution indicates a conversion of about 40% after 4 hours. That conversion results only in the reduction of the nitrile group ($\delta^{11}B$ 23.1 ppm). After a prolonged stirring, a white substance is gradually separated, which cannot be dissolved or distilled.

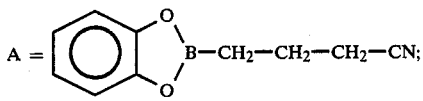

A = B—CH2—CH2—CH2—CN;

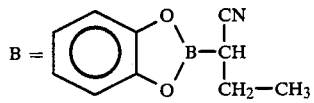

B = B—CH(CN)—CH2—CH3

(D) Catalytic Hydroboronization of Alkynes

A solution of 3.7 g (45 millimoles) 1-hexyne in 5 ml benzene was dropped into a mixture of 5.4 g (45 millimoles) catecholborane and 20.8 mg (0.05 millimoles) ClRh(PPh3)3 in 2.5 ml benzene while the mixture was stirred. After 25 minutes, a distillative separation resulted in a recovery of 4.73 g (52%) hexane-2-yl-1,3,2-benzodioxaborolane, boiling point 79°–60° C. at 0.01 torr, $\delta^{11}B$ 31.1 ppm, $\delta^{1H}$ 7.15–6.82 (5H); 5.74 (1H); 2.3–1.6 (2H); 1.5–1.0 (4H); 1.0–0.7 (3H).

3-hexene-3-yl-1,3,2-benzodioxaborolane was hydroboronized in the same manner. Yield 2.82 g (31%); boiling point 71°–72° C. at 0.01 torr; $\delta^{11}B$ 32.0 ppm; $\delta^1H$: 7.15–6.75 (5H); 2.7–1.7 (4H); 1.3–0.8 (6H).

We claim:

1. A process for producing catecholborane which comprises the step of reacting tris(catecholato)bisborane with an alkali-metal boron hydride selected from the group which consists of lithium borohydride, sodium borohydride and potassium borohydride, in an aliphatic ether organic solvent at room temperature under vigorous agitation, and in which process said alkali-metal boron hydride and said tris(catecholato)bisborane are reacted substantially in a stoichiometric molar ratio of substantially 1:2.

2. The process defined in claim 1 wherein said solvent is selected from the group which consists of diethyl ether, diisopropyl ether, dibutyl ether, dimethyl ether and diethyl ethers of ethylene glycol, diethylene glycol and triethylene glycol and mixtures thereof.

3. The process defined in claim 1 wherein the process is carried out in a dialkyl ether using sodium borohydride or potassium borohydride as the boron hydride, the process further comprising the step of promoting solubilization in said solvent by adding thereto a lithium halide.

4. The process defined in claim 1 wherein the process is carried out in a dialkyl ether, further comprising the step of activating sodium or potassium borohydride by grinding before adding the sodium or potassium borohydride to the solvent.

5. The process defined in claim 1 wherein the process is carried out in a dialkyl ether using sodium or potassium borohydride as said boron hydride, further comprising activating the process by milling.

6. A process for producing catecholborane which comprises the steps of:
 (a) reacting catechol with boric acid or boric acid anhydride in a stoichiometric molar ratio of substantially 3:1 in benzene or toluene under reflux conditions to produce the tris(catecholato)bisborane;
 (b) reacting in an aliphatic ether organic solvent at room temperature under vigorous agitation the tris(catecholato)bisborane with an alkali-metal boron hydride selected from the group which consists of lithium borohydride, sodium borohydride and potassium borohydride in a stoichiometric molar ratio of substantially 1:2 to produce catecholborane in a reaction mixture; and
 (c) recovering the catecholborane from said reaction mixture.

7. The process defined in claim 6 wherein said solvent in step (b) is selected from the group which consists of diethyl ether, diisopropyl ether, dibutyl ether, dimethyl ether and diethyl ethers of ethylene glycol, diethylene glycol and triethylene glycol and mixtures thereof.

8. The process defined in claim 7 wherein step (b) is carried out in a dialkyl ether using sodium borohydride or potassium borohydride as the boron hydride, step (b) further comprising the step of promoting solubilization in said solvent by adding thereto a lithium halide.

9. The process defined in claim 8 wherein step (b) is carried out in a dialkyl ether, further comprising the step of activating sodium or potassium borohydride by grinding before adding the sodium or potassium borohydride to the solvent.

10. The process defined in claim 8 wherein step (b) is carried out in a dialkyl ether using sodium or potassium borohydride as said boron hydride, further comprising activating step (b) by milling.

* * * * *